United States Patent [19]

Siri

[11] Plant 4,920

[45] Nov. 2, 1982

[54] MINIATURE CARNATION

[76] Inventor: Angelo J. Siri, 940 O'Connor St., East Palo Alto, Calif. 94303

[21] Appl. No.: 252,582

[22] Filed: Apr. 9, 1981

[51] Int. Cl.[3] ..... A01H 5/00

[52] U.S. Cl. ..... Plt./70

[58] Field of Search ..... Plt./70

*Primary Examiner*—James R. Feyrer

*Attorney, Agent, or Firm*—Limbach, Limbach & Sutton

[57] ABSTRACT

A sport of 'Moonlight', the instant plant, 'Goldrush', differs therefrom particularly in having anthers and having a goldish toned yellow-orange blossom color.

2 Drawing Figures

1

BACKGROUND OF THE NEW PLANT

This invention comprises a new and distinct miniature carnation variety that has its own set of characteristics that set it apart from all other varieties of miniature carnations. The newly discovered variety, called "Goldrush," originated as a sport of Moonlight, an unpatented variety.

The botanical classification of the new variety is *Dianthus caryophyllus longicaulis.* The commercial classification is Miniature Carnation. The plant takes the form of a bush.

Asexual propagation of the newly discovered miniature carnation variety has been made at Siri Brothers Nursery, Inc. at East Palo Alto, Calif. by taking cuttings. The cuttings so taken and grown, have consistently produced flowers that have the new and distinct characteristics hereinafter described.

DESCRIPTION OF THE DRAWINGS

This new variety of miniature carnation plant is illustrated by the accompanying drawings which show the color characteristics of the flower as nearly true as it is reasonably possible to obtain through conventional photographic procedures.

DESCRIPTION OF THE NEW PLANT

Figure 1:
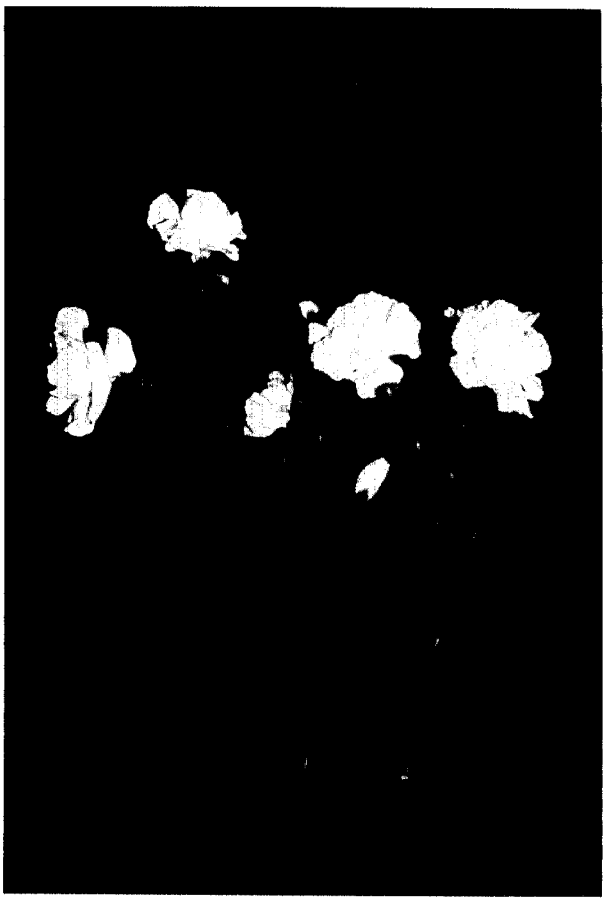
FIG. 1. PRIOR ART
FIG. 1 shows on the right a spray of the new variety "Goldrush," and on the left a spray of the prior Moonlight.
Figure 2:
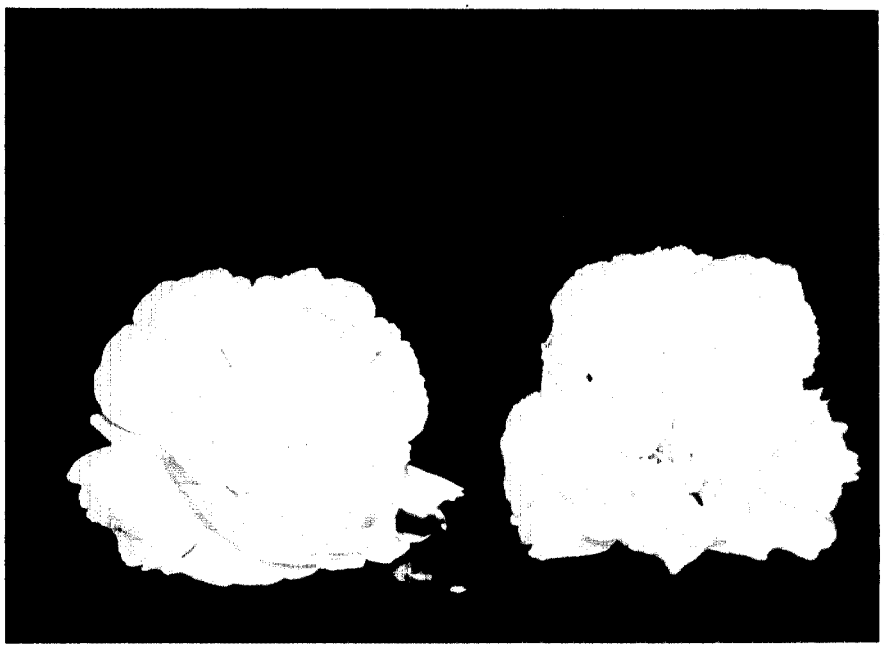
FIG. 2. PRIOR ART
FIG. 2 shows enlarged views of the flowers, Goldrush on the right and Moonlight on the left.

The following detailed description of the new variety is based on my detailed observations of the new cultivar which were made at Siri Brothers Nursery Inc. at 940 O'Connor St., East Palo Alto, Calif. The response time, blooming period, total vigor, and color may vary slightly with varying environmental conditions such as temperature, length of day, and light intensity. The color description is given by designation "H" for hue and "L" for lightness in color chart references designated "LCC" for Limit Color Cascade, Munsell Color, Baltimore, Md. and "RHS" for Royal Horticultural Color Chart, Royal Horticultural Society, London, England.

GROWTH HABITS

Height: Short to medium.

Foliage: Average.

2

Speed of growth: Slower than average — the same as Moonlight.

Root system: Above average — very little loss of plants.

FOLIAGE

Leaf size:

*Length.*—Varies — longer at bottom of stem, shorter at the top. Average at the middle of the stem $4\frac{5}{8}$ inches.

*Width.*—Varies — wider at the bottom of the stem, thinner at the top. Average at the middle of the stem 7/16 of an inch.

*Features.*—N/A.

Leaf shape: Average curl with a long acuminating tip.

Leaf texture: Smooth and leathery.

Leaf color:

*Upperside.*—RHS Green Group 136B with a whitish color over the green.

*Underside.*—RHS Green Group 136B with a whitish color over the green.

Leaf ribs: One rib down the center from the base to the tip of the leaf.

Leaf habit: Average amount of curl.

Leaf density: Average to heavy.

STEM

Stem strength: Strong — better than average.

Stem color: RHS Green Group 136B with a whitish color over the green.

Nodes: Average.

*Space between nodes.*—$3\frac{1}{4}$ inches average at mid-stem.

Stem branching: Very good, wide gaps between branches, not clubby.

BUDS

Bud shape: Oval.

Bud color: Top half LCC H-21 L-14, bottom half LCC H-22 L-9.

Average number of flowering buds per stem: 5.

Uniformity of bud opening: Very uniform.

Bud splitting: Very seldom.

Number of sepals per calyx: 90% of calyxs have 5, and 10% of calyxs have 6.

FLOWER

Description of the color of the bloom: The bloom is a goldfish toned yellow-orange color that is rich and vibrant LCC H-28 L-2. Occasionally, but not often, there is a small streak of white RHS White Group 155D and or a small spot of Pink LCC H-40 L-8 on one and or more of the petals.

General tonality of the color: Bright.

Diameter of average bloom: Approximately 2¼".

Bloom shape: Generally round with a high center and flat outer petals.

Keeping quality: Average.

Fragrance: Slight.

PETALAGE

Petal texture: Soft and smooth.

Petal edge: Slight seration.

Petal color: LCC H-28 L-2.

Color stability: Excellent, there is only a very slight reversion to Moonlight.

Petal size:

*Average length.*—1¾ inches.

*Average width at widest point.*—1 inch.

Calyx color: Top half is LCC H-21 L-14, bottom half is LCC H-22 L-9, the tips of the leaves on the bottom of the calyx are LCC H-22 L-15.

REPRODUCTIVE ORGANS

Stamen: With anthers.

Average length of stamen: 1 inch.

Color of anthers: LCC H-27 L-1.

Color of filament: LCC H-22 L-1.

Pistils:

*Shape.*—Approximately 95% have 2 styles, 5% have 1 style.

*Number.*—One.

*Length from tip to ovary.*—1⅝ inches.

Stigma:

*Shape.*—Round.

*Color.*—White. It is located at the very tip of the style.

Style:

*Color.*—LCC H-26 L-1.

Ovary:

*Shape.*—Ovid.

*Color.*—Tip is LCC H-26 L-11, the top half is LCC H-23 L-9, the bottom half is LCC H-23 L-1.

*Length.*—½ inch.

*Width.*—5/16 inch.

DISTINGUISHING CHARACTERISTICS BETWEEN THE NEW VARIETY AND PARENT

The most distinguishing characteristic between Goldrush and Moonlight is the color itself. Moonlight is a pale yellow while goldrush is a goldish toned yellow-orange. The bottom portion of Moonlight's calyx is lighter than that of Goldrush. 40–50% of Moonlight's stamen have no anthers while all of Goldrushes' stamen have anthers.

SIMILAR CHARACTERISTICS OF THE NEW VARIETY AND PARENT

All of the characteristics of both varieties are similar except for the distinguishing characteristics referred to above.

I claim:

1. A new and distinct carnation cultivar as described and illustrated.

* * * * *